(12) United States Patent
Petrucci

(10) Patent No.: US 9,457,051 B2
(45) Date of Patent: Oct. 4, 2016

(54) USE OF STEM CELLS OR PROGENITOR CELLS TO TREAT, DELAY, PREVENT, OR REPAIR TEARING OF CRUCIATE LIGAMENTS

(71) Applicant: ANIMAL CELL THERAPIES, INC., San Diego, CA (US)

(72) Inventor: Kathryn Petrucci, La Jolla, CA (US)

(73) Assignee: Animal Cell Therapies, Inc., San Diego, CA (US)

(*) Notice: Subject to any disclaimer, the term of this patent is extended or adjusted under 35 U.S.C. 154(b) by 0 days.

(21) Appl. No.: 14/161,291

(22) Filed: Jan. 22, 2014

(65) Prior Publication Data

US 2014/0205574 A1 Jul. 24, 2014

Related U.S. Application Data

(60) Provisional application No. 61/755,161, filed on Jan. 22, 2013.

(51) Int. Cl.
*A01N 63/00* (2006.01)
*A01N 65/00* (2009.01)
*A61K 35/28* (2015.01)

(52) U.S. Cl.
CPC ..................................... *A61K 35/28* (2013.01)

(58) Field of Classification Search
None
See application file for complete search history.

(56) References Cited

U.S. PATENT DOCUMENTS

2002/0005205 A1* 1/2002 Barry et al. .................. 128/898

OTHER PUBLICATIONS

Amoczky et al., "Biomechanical Evaluation of Anterior Cruciate Ligament Repair in the Dog: An Analysis of the Instant Center of Motion", *J. Am. Anim. Hosp. Assoc.*, 1 977 ,13:553-558.
Andriacchi et al., "A Framework for the in Vivo Pathomechanics of Osteoarthritis at the Knee", Ann. *Biomed. Eng.*, 2004, 23(3):447-457.
Aragon et al., "Applications of Evidence-Based Medicine: Cranial Cruciate Ligament Injury Repair in the Dog", *Vet Surg*, 2005, 34(2):93-98.
Bennett et al., "A Reappraisal of Anterior Cruciate Ligament Disease in the Dog", *J. Small. Anim. Pract.*, 1988, 29:275-297.
Brown et al., "Development and Psychometric Testing of an Instrument Designed to Measure Chronic Pain in Dogs with Osteoarthritis", *Am. J. Vet. Res.*, 2007, 68(6):631-637.
Conzemius et al., "Effect of Surgical Technique on Limb Function After Surgery for Rupture of the Cranial Cruciate Ligament in Dogs", *J. Am. Vet. Med. Assoc.*, 2005, 226(2):232-236.
Cook et al., "Proposed Definitions and Criteria for Reporting Time Frame, Outcome, and Complications for Clinical Orthopedic Studies in Veterinary Medicine", *Vet. Surg.*, 2010, 39(8):905-908.
de Bruin et al., "Radiographic Assessment of the Progression of Osteoarthrosis in the Contralateral Stifle Joint of Dogs With a Ruptured Cranial Cruciate Ligament", *Vet. Rec.*, 2007, 161:745-750.

Di Nicola et al., "Human Bone Marrow Stromal Cells Suppress T-Lymphocyte Proliferation Induced by Cellular or Nonspecific Mitogenic Stimuli", *Blood*, 2002, 99:3838-3843.
Doverspike et al., "Contralateral Cranial Cruciate Ligament Rupture: Incidence in 114 Dogs", *J. Am. Anim. Hosp. Assoc.*, 1993, 29:167-170.
Duval et al., "Breed, Sex, and Body Weight as Risk Factors for Rupture of the Cranial Cruciate Ligament in Young Dogs", *J. Am. Vet. Med. Assoc.*, 1999, 215(6):811-814.
Elkins et al., "A Retrospective Study Evaluating the Degree of Degenerative Joint Disease in the Stifle Joint of Dogs Following Surgical Repair of Anterior Cruciate Ligament Rupture", *J. Am. Anim. Hosp. Assoc.*, 1991, 27:533-540.
Griffon, "A Review of the Pathogenesis of Canine Cranial Cruciate Ligament Disease as a Basis for Future Preventive Strategies", *Vet. Surg.*, 2010, 39:399-409.
Hayashi et al., "Cranial Cruciate Ligament Pathophysiology in Dogs With Cruciate Disease: A Review", *J. Am. Anim. Hosp. Assoc.*,2004, 40:385-390.
Hudson et al., "Assessing Repeatability and Validity of a Visual Analogue Scale Questionnaire for Use in Assessing Pain and Lameness in Dogs", *Am. J. Vet. Res.*, 2004, 65(12):1634-1643.
Johnson et al., "Incidence of Canine Appendicular Musculoskeletal Disorders in 16 Veterinary Teaching Hospitals from 1980 through 1989", *Vet. Camp. Orthap. Traumatol.*, 1994, 7:56-69.
Kim et al., Effect of Tibial Tuberosity Advancement on Femorotibial Contact Mechanics and Stifle Kinematics, *Vet. Surg.*, 2009, 38:33-39.
Kim et al., "Tibial Osteotomies for Cranial Cruciate Ligament Insufficiency in Dogs", *Vet. Surg.*, 2008, 37:111-125.
Korvick et al., "Three-Dimensional Kinematics of the Intact and Cranial Cruciate Ligament-Deficient Stifle of Dogs", *J. Biomech.*, 1994, 27(1):77-87.
Pozzi et al., "Ex vivo Pathomechanics of the Canine Pond-Nuki Model", PLOS One, 2013, 8 ( 12) :e81383:1-6.
Proceedings of the 35th Annual Conference of the Veterinary Orthopedic Society, Big Sky, MT, Mar. 8-15, 2008, pp. 1-93.
Tashman et al., "Kinematics of the ACL-Deficient Canine Knee During Gait: Serial Changes Over Two Years", *J. Orthop. Res.* 2004, 22(5):931.
Tonks et al., "A Review of Extra-Articular Prosthetic Stabilization of the Cranial Cruciate Ligament-Deficient Stifle", *Vet. Camp. Orthop. Traumatol.*, 2010, 24(3):167-177.
Tonks et al., "The Effects of Extra-Articular Suture Tension on Contact Mechanics of the Lateral Compartment Stifles Treated with the TightRope CCL® or Lateral Suture Technique", *Vet. Surg.*, 2010, 39:343-349.
Vasseur, "Clinical Results Following Nonoperative Management for Rupture of the Cranial Cruciate Ligament in Dogs", *Vet. Surg.*, 1984, 13:243.
Whitehair et al., "Epidemiology of Cranial Cruciate Ligament Rupture in Dogs", *J. Am. Vet. Med. Assoc.*, 1993, 203:1016-1019.

* cited by examiner

*Primary Examiner* — Thomas J Visone
(74) *Attorney, Agent, or Firm* — Pillsbury Winthrop Shaw Pittman LLP

(57) ABSTRACT

Methods for treating a partial or complete rupture of cranial cruciate ligament (CrCL) damage and for preventing or delaying CrCL damage with or without synovitis in dogs are disclosed. For example, this document provides methods for using stem cells and/or progenitor cells to prevent or reduce the likelihood of CrCL rupture in the contralateral leg of mammals, especially dogs, diagnosed with CrCL rupture, as well as methods for using stem cells and/or progenitor cells to treat, delay or prevent complete CrCL rupture in mammals, especially dogs, diagnosed as having a partial CrCL rupture.

7 Claims, No Drawings

USE OF STEM CELLS OR PROGENITOR CELLS TO TREAT, DELAY, PREVENT, OR REPAIR TEARING OF CRUCIATE LIGAMENTS

CROSS REFERENCE TO RELATED APPLICATION(S)

This application claims priority to U.S. Provisional Patent Application No. 61/755,161, filed Jan. 22, 2013, entitled "USE OF STEM CELLS OR PROGENITOR CELLS TO TREAT, DELAY, PREVENT, OR REPAIR TEARING OF CRUCIATE LIGAMENTS", the disclosure of which is incorporated by reference.

TECHNICAL FIELD

This disclosure relates to methods for treating, delaying and/or preventing cranial cruciate ligament (CrCL) damage in mammals, and more specifically, dogs. For example, this disclosure relates to methods for using stem cells to treat partial or complete CrCL ruptures and to prevent or reduce the likelihood of CrCL rupture, such as in the contralateral leg of dogs diagnosed with unilateral CrCL rupture.

BACKGROUND

CrCL rupture is the most common cause of hind limb lameness in dogs, and can precipitate meniscal injury and inevitably incite osteoarthritis (OA) of the stifle (Johnson et al., *Vet Comp Orthop Traumatol*, 7:56-69, 1994; and Elkins et al., *J Am Anim Hosp Assoc* 27:533-540, 1991). Adult, large breed dogs (e.g., Rottweilers, Newfoundlands, and American Staffordshire terriers) are most frequently affected by CrCL rupture (Bennett et al., *J Small Anim Pract* 29:275-297, 1988; Duval et al., *J Am Vet Med Assoc*, 215(6):811-814, 1999; and Whitehair et al., *J Am Vet Med Assoc*, 203:1016-1019, 1993). Although the risk for CrCL rupture increases with age, many large breed dogs succumb to this condition in young adulthood. There is a growing body of evidence that cruciate ligament disease in a certain population of dogs is caused by a biologic or inflammatory process that promotes the gradual failure of the cruciate ligament over time.

SUMMARY

Up to 60% of dogs with unilateral CrCL rupture will rupture the CrCL in the contralateral limb within one year. This gradual degradation of the cruciate ligament is thought to be the result of an underlying synovitis that weakens the ligament over time. This disclosure is based in part on the development of a therapy that includes injection of stem cells such as mesenchymal stem cells and/or progenitor cells (MSCs) intravenously or into the intra-articular stifle of a dog for the treatment of a partial or complete CrCL rupture, or intravenously or into the intra-articular stifle of dogs at risk for a CrCL rupture, such as into the contralateral intra-articular stifle of dogs diagnosed with unilateral CrCL rupture. Mesenchymal stem cells have been studied for their anti-inflammatory, immune modulating and repair effects. While not intending to be bound by theory, the methods described herein may have a significant impact on the care of dogs at risk of CrCL insufficiency by immune modulation, decreases in inflammatory mediators and cytokines and repair of micro tears. For example, the use of intra-articular MSC injection to delay or prevent the onset of contralateral CrCL rupture may mean that millions of dogs will not have to go through costly and risky surgical procedures.

Various embodiments include methods for reducing the likelihood of CrCL rupture, or delaying or preventing a CrCL rupture, in a dog at risk for a rupture, including a dog diagnosed with an existing or previous unilateral CrCL rupture. The method may reduce the likelihood of, delay or prevent a complete rupture of the CrCL or may reduce the likelihood of, delay, or prevent a partial rupture of the CrCL. Other embodiments include treatment of an existing partial or complete rupture of the CrCL. The methods include administering a composition comprising stem cells such as mesenchymal stem cells (MSCs) and/or progenitor cells to an affected leg and/or intravenously for treatment of an existing partial or complete CrCL rupture, or to an unaffected leg at risk for CrCL damage, such as the contralateral leg of a dog having been diagnosed with a CrCL rupture. The composition may be administered to the area of the CrCL in the affected or contralateral leg.

The MSCs and/or progenitor cells may be autologous or allogeneic. They may be administered by injection into the affected or contralateral knee joint of the dog. The number of injected cells may be between about $1 \times 10^6$ and about $5 \times 10^8$ MSCs and/or progenitor cells. In some embodiments, one or more subsequent doses of a composition containing MSCs and/or progenitor cells may be administered after the first administering step, such as between about 15 days and about 1 year after the first administration.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

There are two cruciate ligaments in the canine knee joint: the cranial cruciate ligament (CrCL) and the caudal cruciate ligament (CaCL). The same ligaments are present in human knees, except they are called the anterior cruciate ligament (ACL) and the posterior cruciate ligament (PCL), respectively. The CrCL/ACL is most commonly injured in both dogs and people. In contrast to people, where ACL rupture is almost always caused by trauma, CrCL rupture in dogs is most commonly due to progressive, degenerative failure, whereas traumatic tears are rare (Hayashi et al., *J Am Anim Hosp Assoc* 40:385-390, 2004). The risk of contralateral CrCL rupture is between 40% and 60% within 12-17 months of diagnosis (de Bruin et al., *Vet Rec*, 161:745-750, 2007; and Doverspike et al., *J Am Anim Hosp Assoc* 29:167-170, 1993), increasing to over 60% rupture with early radiographic changes.

CrCL rupture has multiple effects on stifle biomechanics (Arnoczky et al., *J Am Anim Hosp Assoc*, 13:553-558, 1977; Korvick et al., J Biomech 27(1):77-87, 1994; Tashman et al.,

*J Orthop Res* 22(5):931, 2004; and Andriacchi et al., *Ann Biomed Eng* 23(3):447-457, 2004). For example, CrCL deficiency results in cranial tibial translation, increased internal rotation, and adduction of the tibia, especially during weight-bearing. The abnormal alignment between the bones occurring in the CrCL-deficient stifle alters loading of the articular cartilage, which may be an initiating factor in the development of OA (Andriacchi et al., supra; and Pozzi et al., "In vitro pathomechanics of the Pond-Nuki Model," Proceedings of the 35th Annual Conference of the Veterinary Orthopedic Society, Big Sky, Mont.,: 31.16, March 2008).

A number of surgical techniques can be used to address CrCL rupture, including intra-articular stabilization, extra-articular stabilization, and tibial osteotomy techniques (Tonks et al., *Vet Comp Orthop Traumatol*, 24(3):167-177, 2010; and Kim et al., *Vet Surg*, 37:111-125, 2008). Such stabilization techniques fail to prevent OA from developing, however, and none completely restore normal function (Kim et al., *Vet Surg*, 38(1):33-39, 2009; Kim et al., *Vet Surg*, 38(1):23-32, 2009; Tonks et al., *Vet Surg*, 39(3):343-349, 2010; Aragon and Budsberg, *Vet Surg*, 34(2):93-98, 2005; Vasseur, *Vet Surg*, 13:243, 1984; and Conzemius et al., *J Am Vet Med Assoc*, 226(2):232-236, 2005). Thus, emphasis on preventive measures of CrCL rupture, rather than treatment, may be useful (Griffon, *Vet Surg*, 39:399-409, 2010).

Mesenchymal stem cells (MSCs) are multipotential non-hematopoietic progenitor cells that can be differentiated into various lineages, such as bone, cartilage, and adipose tissue (Di Nicola et al., *Blood*, 99:3838-3843, 2002). MSCs can be isolated from the bone marrow, adipose tissue, umbilical cord tissue, synovial fluid, ligament and tendon structures, placenta, teeth, of mammals, including, without limitation, canine, equine, porcine, and feline and human species. MSCs may be a therapeutic tool for regenerative medicine based on their ability to migrate to damaged tissue, engraft, undergo differentiation, as well as their anti-inflammatory and immunomodulatory properties. Other types of stem cells may also be used in the various embodiments described herein rather than mesenchymal stem cells, including embryonic stem cells, fetal stem cells, and induced pluripotent stem cells (iPSs).

Progenitor cells are early descendants of stem cells that can differentiate to form one or more kinds of cells, but cannot divide and reproduce indefinitely. A progenitor cell is often more limited than a stem cell in the kinds of cells it can become.

As described herein, either MSCs and/or progenitor cells may be useful for treating a partial or complete CrCL rupture or for preventing or delaying CrCL rupture in dogs, such as dogs at genetic risk for a CrCL rupture or a risk of contralateral CrCL rupture. Dogs at risk for CrCL rupture include, but are not limited to, dogs with a high risk of CrCL rupture in the breed, with a family history or CrCL rupture, and with a previous unilateral CrCL rupture in the contralateral leg. For example, dogs presenting with a unilateral CrCL rupture or with a previous unilateral CrCL rupture may benefit from immune modulatory, anti-inflammatory and reparative effects of intra-articular injection(s) of MSCs and/or progenitor cells in the contralateral stifle, which may reduce the likelihood of CrCL rupture in the contralateral limb into which the cells are injected, or may delay or prevent the onset of CrCL rupture in the contralateral limb. In addition, MSCs and/or progenitor cells may be useful for treating partial CrCL rupture and for preventing or delaying complete CrCL rupture in dogs with partial CrCL rupture. For example, dogs presenting with partial tear of the CrCL may benefit from intra-articular injection of MSCs and/or progenitor cells in the affected stifle, which may prevent, delay, or reduce the likelihood of further damage to the CrCL in the treated leg and may promote partial or complete repair of the torn ligament. Such treatment may be provided in lieu of surgical repair or in addition to surgical repair of a partial or complete CrCL tear. For example, the MSCs and/or progenitor cells may be administered prior to, at the time of, and/or after the surgical repair of the CrCL to promote improved healing of the CrCL.

Thus, in some embodiments, this disclosure provides methods for treating, preventing, delaying, or reducing the likelihood of CrCL rupture. The methods can include administering to the affected leg and/or the contralateral leg a composition containing MSCs and/or progenitor cells, where the composition is administered intravenously and/or to the area of the ipsilateral or contralateral CrCL (e.g., into the knee joint). This disclosure also provides methods of treating including repairing the CrCL of dogs having a partial or complete CrCL rupture as well as preventing, delaying, or reducing the likelihood of worsening or complete CrCL rupture in the affected limb of a dog having partial CrCL rupture. Such methods can include administering to the affected leg and/or intravenously a composition containing MSCs and/or progenitor cells, where the composition is administered to the area of the affected CrCL and/or intravenously.

The administration of the MSCs and/or the progenitor cells in the methods provided herein can be via injection, such as intravenous or intra-articular injection, although any other suitable route of administration also can be used. In some embodiments, the MSCs and/or progenitor cells are autologous. For example, MSCs and/or progenitor cells can be obtained from a dog prior to surgical treatment for CrCL rupture, at the time of surgical treatment for CrCL rupture, or at a follow up visit after surgery. Alternatively, the MSCs and/or progenitor cells are allogeneic, and are obtained from any dog, such as a healthy dog that does not show signs of CrCL damage. The MSCs and/or progenitor cells can be obtained from bone marrow or from any other suitable source within the donor animal such as umbilical cord tissue, placenta, adipose tissue, synovial fluid, ligament or tendon structure, and teeth.

After a sample containing MSCs and/or progenitor cells is obtained from the donor animal, whether the cells are autologous or allogeneic, the sample can be processed to isolate and expand the MSCs and/or progenitor cells. For example, cells can be maintained, evaluated, and cultured as described in the Examples herein, in preparation for administration to a recipient. Prior to administration, the cells can be suspended in a suitable carrier such as saline, hyaluronic acid or plasma, for example. The carrier media may be any media that is biologically compatible with the cells and with the recipient. For example, the carrier may include one or more of plasma, saline, a balanced salt solution such as phosphate buffered saline, hyaluronic acid, collagen sugar chitosan, gelatin, fibronectin, Matrigel, or another extracellular matrix material.

Various embodiments include administering one or more other agents to modify the microenvironment to assist in the repair and/or strengthening of the CrCL. Such agents may be delivered concurrently with the MSCs and/or progenitor cells, such as in the same composition, or may be delivered separately as a separate composition that may be administered at generally the same time as the MSCs and/or progenitor cells, or at a different time such as before or after administration of the MSCs and/or progenitor cells. For example, in some embodiments, the agents may be administered to the dog in order to modify or improve the microenvironment prior to administration of the MSCs and/or progenitor cells. Examples of agents that may be used to modify the microenvironment include one or more steroids, non-steroidal anti-inflammatory agents (NSAIDS), hyaluronic acid, antibodies, growth factors, cytokines, genetic agents such as micro RNA, siRNA, shRNA, and/or small molecules.

A MSC-containing composition or progenitor cell containing composition can be administered to the affected leg or to the contralateral leg (e.g., to the knee joint) using any suitable method, including injection. The composition can be administered in an amount that contains about $1\times10^6$ to about $5\times10^8$ MSCs and/or progenitor cells to the dog, for example. The MSCs and/or progenitor cells can be administered to the affected leg and/or to the contralateral leg of the animal prior to surgical repair of the ruptured CrCL, at the time the ruptured CrCL is repaired, at any time after repair of the ruptured CrCL, or at any time cruciate ligament disease or synovitis presents itself either by changed clinical signs, in synovial fluid biomarkers or inflammatory indicators or by detection through imaging. For example, a composition containing MSCs and/or progenitor cells can be administered to the contralateral leg within about a week of surgery to repair the ruptured CrCL, or any time thereafter (e.g., 1 day, 2 days, 3 days, 4 days, days, 5 days, 6 days, 1 week, 2 weeks, 1 month, 2 months, 3 months, 4 months, 6 months, 1 year, or more than 1 year after surgery). In some embodiments, the MSCs and/or progenitor cells are administered to both the affected leg and the contralateral leg at the same time, such as at the time of surgical repair of the affected leg, and/or at different times as indicated by synovial fluid inflammatory biomarkers, imaging studies or clinical signs.

The methods provided herein also can include administering one or more subsequent doses of the MSC-containing composition and/or progenitor cell containing composition to the dog, at one or more intervals after the first administering step, in the affected leg and/or in the contralateral leg. For example, a second dose of MSCs and/or progenitor cells can be administered to a dog about 0.5 month to about 1 year (e.g., about 14 days, about 30 days, about 45 days, about 60 days, about 75 days, about 90 days, about 120 days, about 150 days, about 180 days, or about 365 days), or between about 30 days and about 90 days, after the first administration. In some cases, further doses also can be administered. In some embodiments, multiple doses, such as two, three, four, or more doses, are administered at periodic intervals, such as every 3 weeks, every 3 months, every 6 months, or every year for the desired number of doses.

Treatment as described herein can be effective to treat or assist in the repair of partial CrCL rupture, and to prevent rupture of the CrCL in dogs at risk for CrCL rupture, such as dogs having a previous CrCL rupture, to delay rupture of the contralateral CrCL, or to reduce the likelihood that the contralateral CrCL will rupture, as compared to a control animal (or a population of control animals), such as an animal treated for unilateral CrCL rupture without preventative treatment of the contralateral knee. Treatment also can be effective to prevent, delay, or reduce the likelihood of complete rupture of a partially ruptured CrCL, as compared to a control animal (or a population of control animals) not treated for partial CrCL rupture.

The invention will be further described in the following examples, which do not limit the scope of the invention described in the claims.

EXAMPLES

Example 1

Determining whether stem cell and/or progenitor cell therapy delays the onset of CrCL rupture in dogs Dogs undergoing surgical treatment for unilateral CrCL rupture are identified for inclusion in a study to determine whether MSC and/or progenitor cell therapy is a successful preventive measure against CrCL rupture. At the outset of the study, the use of stem cells alone, progenitor cells alone, or a combination of stem cells and progenitor cells, will be selected as the treatment for all dogs in the study group. Half of the dogs receive intra-articular MSC and/or progenitor cell injections in the contralateral normal (unaffected) limb, and the other half receive placebo injections (e.g., of sterile saline). To measure the success of treatment, dogs are monitored for the development of CrCL rupture in the unaffected limb. A combination of subjective (e.g., quality of life) and objective (e.g., limb function as measured by limb kinetics) outcome measures are used to test the hypotheses that (1) as compared to dogs receiving placebo, a lower percentage of dogs treated with intra-articular MSCs and/or progenitor cells develop CrCL rupture in the unaffected limb, (2) dogs treated with intra-articular MSCs and/or progenitor cells have significantly greater client-based scores on quality of life questionnaires, and (3) dogs treated with intra-articular MSCs and/or progenitor cells have significantly better limb function.

Experimental animals: Privately owned dogs with a body weight of 25-35 kg are enrolled after informed consent by their owners. A medical history is obtained from the owner for each dog. The dogs undergo an orthopedic exam and radiographic examination of the stifle.

Inclusion criteria: Adult dogs (2-10 years of age) presenting for unilateral lameness and undergoing tibial plateau leveling osteotomy (TPLO) and arthroscopy are identified. A definitive diagnosis of unilateral CrCL rupture is made using physical exam, radiographs and arthroscopy. Only dogs without orthopedic disease other than unilateral CrCL rupture are included.

Study design: Dogs enrolled in the study are randomly allocated to a cohort undergoing intra-articular injection of MSC and/or progenitor cells or intra-articular injection of saline.

MSC source: MSC and/or progenitor cells are obtained from either dog bone marrow or umbilical cord sources.

Treatment with intra-articular injection of MSC and/or progenitor cells or placebo: MSC and/or progenitor cells are injected at the time of the initial surgery and then every three months for the duration of the study. The dogs are sedated and after flushing the joint with saline, either MSCs and/or progenitor cells or saline is injected. The clinician is blind to the injected treatment.

Data collection: The primary outcome is the presence or absence of CrCL rupture at the 18 month recheck, based on arthroscopic evaluation. Clinical outcomes are defined using two owner questionnaires: the Canine Brief Pain Inventory (Brown et al., *Am J Vet Res,* 68(6):631-637, 2007) and the Canine Movement Assessment Visual Analog Scale (Hudson et al., *Am J Vet Res,* 65(12):1634-1643, 2004). Minor and major complications are reported (Cook et al., *Vet Surg,* 39(8):905-908, 2010). Onset or progression of CrCL disease is documented with arthroscopy. Limb function is measured by force plate analysis.

Data analysis: A statistician is consulted for study design, sample size and data analysis. A chi-squared test is used to compare the two proportions.

Pre-study power analysis: Based on a power analysis performed using a 40% incidence of contralateral CrCL disease within the first year, 40 dogs per group are required to detect a 66% decrease in the incidence of contralateral CrCL rupture, with alpha set at 0.05 and power of 0.8. A pilot study with 20 dogs (10 per group) is initially conducted.

Example 2

Determination of whether therapy using BM-MSCs and/or progenitor cells will improve clinical outcome and aid in healing of ruptured CrCL for dogs with partial rupture of the cruciate ligament.

This study is conducted to investigate the efficacy of umbilical cord tissue derived mesenchymal and/or progenitor cells for treatment of dogs with partial rupture of the cruciate ligament. At the outset of the study, the use of stem cells alone, progenitor cells alone, or a combination of stem cells and progenitor cells, will be selected as the treatment for all dogs in the study group.

Recruitment: Dogs with suspected cruciate disease are admitted for clinical evaluation. A relevant history is obtained from the owner and/or the referring DVM (RDVM). Dogs, all having partial cranial cruciate rupture, are enrolled in the study. To be eligible, dogs are to be cared for by attentive owners who agree by informed consent to participate in the study, to follow a set schedule of veterinary appointments, and to observe their dog for the entire study period. Only dogs without orthopedic disease other than CrCL rupture are included.

Diagnostic plan: A diagnosis of partial cruciate rupture is confirmed based on physical examination, lameness evaluation, arthrocentesis, MRI and radiographs. A standard diagnostic protocol will be followed for each patient. Advanced diagnostic tests to document partial rupture of the CrCL (arthroscopic evaluation and CT with positive contrast or MRI if available) are performed pre and post treatment (post treatment at 30 and 60 days) as part of the investigation of efficacy for both the affected and unaffected stifle.

Consent and owner involvement: Each owner signs a consent form when their dog is enrolled in the study. The consent form involves a discussion about potential risks and discomforts to the animal, including the fact that the treatment is still considered experimental. Owners also complete a questionnaire that determines subjective evaluation of the animals at home and owner satisfaction.

Study design: Dogs confirmed to have a partial cruciate rupture are admitted into the study. Dogs on concomitant therapy, such as NSAIDs, are required to be on those medications for at least 5 days before enrollment in the study, and to remain on the drugs at the same level throughout the study. Alternative treatments such as chiropractic and acupuncture, if used, are discontinued in all dogs at least 10 days before enrollment in the study. At the time of enrollment, dogs are trained to walk and trot across a force plate so that objective measurements can be obtained before and after treatment, along with subjective evaluation in the form of a questionnaire completed by the client. Objective force plate values include ground reaction forces and stance times. Velocity and acceleration for each pass also are determined. A digital video recorder is used to record the trials, and digitalized images are evaluated to verify the valid trials. Other diagnostics for evaluation are conducted as described above.

Cell based therapy: Three to five million allogeneic umbilical cord tissue derived mesenchymal cells are injected into the stifle joint, depending on the body weight of the dog. Cells will have been labeled with an Ion Particle which is visible on MRI.

Progenitor cells may be used alternatively or in addition to umbilical cord derived mesenchymal stem cells.

At this time the dog is returned to the veterinary facility. The owners are asked to hold the dog off feed for a period of 12 hours. The prepared MSCs and/or progenitor cells in the saline or plasma carrier (or plasma alone for placebo) are brought to the induction area, and the dog is prepared for aseptic injection of the cells or placebo plasma into the affected joint. Joints are injected through routine arthrocentesis approaches. A total number of 5-10 million cells per joint, in 1 mL or less total volume are used for each. Postoperative care instructions are standardized for all dogs of the study, and involve restriction of activity to leash walks for a period of 8 weeks.

Evaluation of efficacy: Dogs are followed for a period of 12 months to assess long-term response and incidence of complete cruciate rupture following treatment. Complete physical exams, orthopedic exams, and force plate evaluations are conducted at each visit. Joint fluid evaluation is assessed prior to treatment, at the time of each stem cell injection, and at the time of the MRI scan at 6 weeks post initiation of treatment. Synovial fluid is stored at $-80°$ C. or below $-20°$ C. if the sample is not to be evaluated right away. Cytology analyses typically are conducted on the same day; samples collected for IR or biomarker evaluation are stored at $-80°$ C. until analysis.

Dogs are evaluated using the force plate prior to treatment, at each treatment visit, and at 6 weeks and 12 weeks post initiation of treatment. Values for peak vertical force at consistent velocity are compared for each visit. In some cases, blood is collected and run for CBC/chem analysis at 6 weeks and 12 weeks.

MRI evaluation of the stifle is performed prior to initiation of treatment and at the 6-week post treatment visit. The treated leg and contralateral leg are both evaluated. The weight bearing for each leg also is evaluated before and after treatment, as this data can be a good indication for further development.

In addition, client evaluation and satisfaction are assessed using responses to the questionnaires.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for reducing the likelihood of cranial cruciate ligament (CrCL) rupture in a contralateral normal, unaffected leg of a dog diagnosed with an existing or previous unilateral CrCL rupture, or stifle synovitis with or without instability in an opposing leg, the method comprising administering a composition comprising mesenchymal stem cells (MSCs) or progenitor cells to the contralateral normal, unaffected leg of the dog, wherein the composition is administered either intravenously or directly into an area of the CrCL in the contralateral leg.

2. The method of claim 1, wherein the MSCs and/or progenitor cells are autologous.

3. The method of claim 1, wherein the MSCs and/or progenitor cells are allogeneic.

4. The method of claim 1, wherein the composition is administered by injection into the contralateral knee joint of the dog.

5. The method of claim 1, comprising administering about $1\times10^6$ to about $5\times10^8$ MSCs and/or progenitor cells to the dog.

6. The method of claim 1, further comprising administering a subsequent dose of an MSC-containing composition at one or more intervals after the first administering step.

7. The method of claim 6, wherein a subsequent dose of the MSC-containing composition is administered about 15 days to about 1 year after the first administration.

\* \* \* \* \*